(12) United States Patent
VanWiggeren

(10) Patent No.: US 7,817,278 B2
(45) Date of Patent: Oct. 19, 2010

(54) SURFACE PLASMON RESONANCE SENSOR APPARATUS HAVING MULTIPLE DIELECTRIC LAYERS

(75) Inventor: Gregory D. VanWiggeren, San Jose, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 476 days.

(21) Appl. No.: 11/836,025

(22) Filed: Aug. 8, 2007

(65) Prior Publication Data

US 2009/0040507 A1    Feb. 12, 2009

(51) Int. Cl.
    *G01N 21/55* (2006.01)
(52) U.S. Cl. ....................................... 356/445
(58) Field of Classification Search .................. 356/445
    See application file for complete search history.

(56) References Cited

U.S. PATENT DOCUMENTS

| | | | |
|---|---|---|---|
| 5,606,633 A * | 2/1997 | Groger et al. | 385/12 |
| 5,991,488 A | 11/1999 | Salamon et al. | |
| 6,330,387 B1 | 12/2001 | Salamon et al. | |
| 6,421,128 B1 | 7/2002 | Salamon et al. | |
| 2007/0046943 A1 | 3/2007 | VanWiggeren et al. | |
| 2008/0225293 A1 * | 9/2008 | Ye et al. | 356/364 |

FOREIGN PATENT DOCUMENTS

WO    2006132476    12/2006

OTHER PUBLICATIONS

Wolfgang Knoll—"Interfaces and Thin Films As Seen by Bound Electromagnetic Waves"; Annual Review of Physical Chemistry, Oct. 1998, vol. 49; pp. 569-638.

Wikipedia, The Free Encyclopedia—"Plasmon"; http://en.wikipedia.org/wiki/Plasmon; pp. 1-3.

(Continued)

*Primary Examiner*—Tarifur Chowdhury
*Assistant Examiner*—Michael LaPage

(57) ABSTRACT

A surface plasmon resonance (SPR) spectrometer sensor apparatus for measuring a property of an analyte substance that can be adsorbed on a surface by directing a beam of incident radiation on the apparatus at an incident angle relative thereto, receiving a beam of reflected radiation off the apparatus, and measuring dips in reflected radiation as a function of incident angle or wavelength, the dips being indicative of resonances in the apparatus. The SPR spectrometer comprises a conductive layer having a first side which receives incident radiation, and having a second side opposite to the first side; and a dielectric stack having first and second sides opposite to each other, the first side being in contact with the conductive layer, the second side for receiving an analyte sample to be disposed thereon. The dielectric stack includes a plurality of dielectric layers having respective thicknesses and indices of refraction, each successive one of the plurality of dielectric layers having an index of refraction which is alternatingly higher than, and lower than, the indices of refraction of adjacent ones of the plurality of dielectric layers. The plurality of dielectric layers including a first dielectric layer at the first side of the dielectric stack, and a last dielectric layer at the second side of the dielectric stack, the last dielectric layer having a boundary surface for contacting the received analyte sample, and having an index of refraction so as to achieve total internal reflection (TIR) at the boundary surface.

16 Claims, 4 Drawing Sheets

OTHER PUBLICATIONS

Surface Science Techniques—"SPR—Surface Plasmon Resonance"; Institut Fur Physikalische Chemie der Universitat Tubingen, Germany; p. 1; http://www.uksaf.org/tech/spr.html.

Wikipedia, The Free Encyclopedia—"Surface Plasmon Resonance"; pp. 1-3; http://en.wikipedia.org/wiki/Surface_plasmon_resonance.

INANO—"Surface Plasmon Resonance"; pp. 1-2; http://www.inano.dk/sw2565.asp.

J. Ctyroky, J. Homola and M. Skalsky—"Tuning of Spectral Operation Range of a Waveguide Surface Plasmon Resonance Sensor"; Electronic Letters, Jul. 3, 1997, vol. 33, No. 14; pp. 1246-1248.

* cited by examiner

SURFACE PLASMON RESONANCE SENSOR APPARATUS HAVING MULTIPLE DIELECTRIC LAYERS

BACKGROUND OF THE INVENTION

The invention is related to the physical phenomenon of surface plasmon resonance (SPR).

When light incident on a conductive surface (such as a thin layer or film of metal, typically gold or silver) possesses the proper wavelength, polarization and angle of incidence, the conducting electrons in the metal film oscillate in a resonant manner. This oscillation, together with the associated photon (or polariton electromagnetic (EM) wave) is called a surface plasmon wave. A surface plasmon is a surface electromagnetic wave that propagates along the surface of the metal film. A surface plasmon may be treated as a "quasi-particle", that is, a hybrid of the photon and the electron waves in the material.

The surface plasmon wave absorbs the incident optical energy at the previously mentioned proper wavelength, polarization, and angle of incidence. Because of this absorbance, a radiation sensor may make use of the surface plasmon wave phenomenon. Where incident radiation covers a range of wavelengths, polarizations, and/or angles of incidence, the radiation reflected off the sensor's conductive surface demonstrates an anomalous reduction, or "dip," at the particular values at which the surface plasmon resonance takes place.

Where a layer of material to be analyzed (hereinafter "analyte," "adsorbed material" or "adsorbate") is adsorbed onto the conductive surface, SPR provides an optical method for measuring the refractive index of the adsorbate. The measured refractive index may be used to calculate the mass, thickness, etc., of the adsorbed material. This SPR technique exploits the fact that, at the conditions specified above, surface plasmons on a metallic surface can be excited by photons, thereby transforming the photon into a surface plasmon. The conditions for producing such surface plasmons depend, in part, on the refractive index of the adsorbate.

SUMMARY OF THE INVENTION

A surface plasmon resonance (SPR) spectrometer sensor apparatus for measuring a property of an analyte substance that can be adsorbed on a surface by directing a beam of incident radiation on the apparatus at an incident angle relative thereto, receiving a beam of reflected radiation off the apparatus, and measuring dips in reflected radiation as a function of incident angle or wavelength, the dips being indicative of resonances in the apparatus. The SPR spectrometer comprises a conductive layer having a first side which receives incident radiation, and having a second side opposite to the first side; and a dielectric stack having first and second sides opposite to each other, the first side being in contact with the conductive layer, the second side for receiving an analyte sample to be disposed thereon. The dielectric stack includes a plurality of dielectric layers having respective thicknesses and indices of refraction, each successive one of the plurality of dielectric layers having an index of refraction which is alternatingly higher than, and lower than, the indices of refraction of adjacent ones of the plurality of dielectric layers. The plurality of dielectric layers including a first dielectric layer at the first side of the dielectric stack, and a last dielectric layer at the second side of the dielectric stack, the last dielectric layer having a boundary surface for contacting the received analyte sample, and having an index of refraction so as to achieve total internal reflection (TIR) at the boundary surface.

Further features and advantages of the present invention, as well as the structure and operation of preferred embodiments of the present invention, are described in detail below with reference to the accompanying exemplary drawings.

DETAILED DESCRIPTION

In the discussion which follows, the surface plasmon resonance phenomenon, and examples of apparatus embodying the invention, will be set forth and explained in terms of incident "light," etc. It will be understood, however, that this is not limiting as to any particular range of wavelengths such as the visible light spectrum. Rather, where "light" is referred to, it will be understood that other wavelengths of electromagnetic radiation also fall within the spirit and scope of the invention, and of the embodiments that are described.

Analyte Directly on Metal Layer

Conventional surface plasmon resonance (SPR) spectrometers can be used to detect variations in either the refractive index (hereinafter also called "index of refraction" or simply "index"; plural: "indices") near the sensor surface These systems typically comprise a sensor apparatus having a metal film deposited either on a diffraction grating or on a prism (the Kretschmann configuration).

Figure 1:
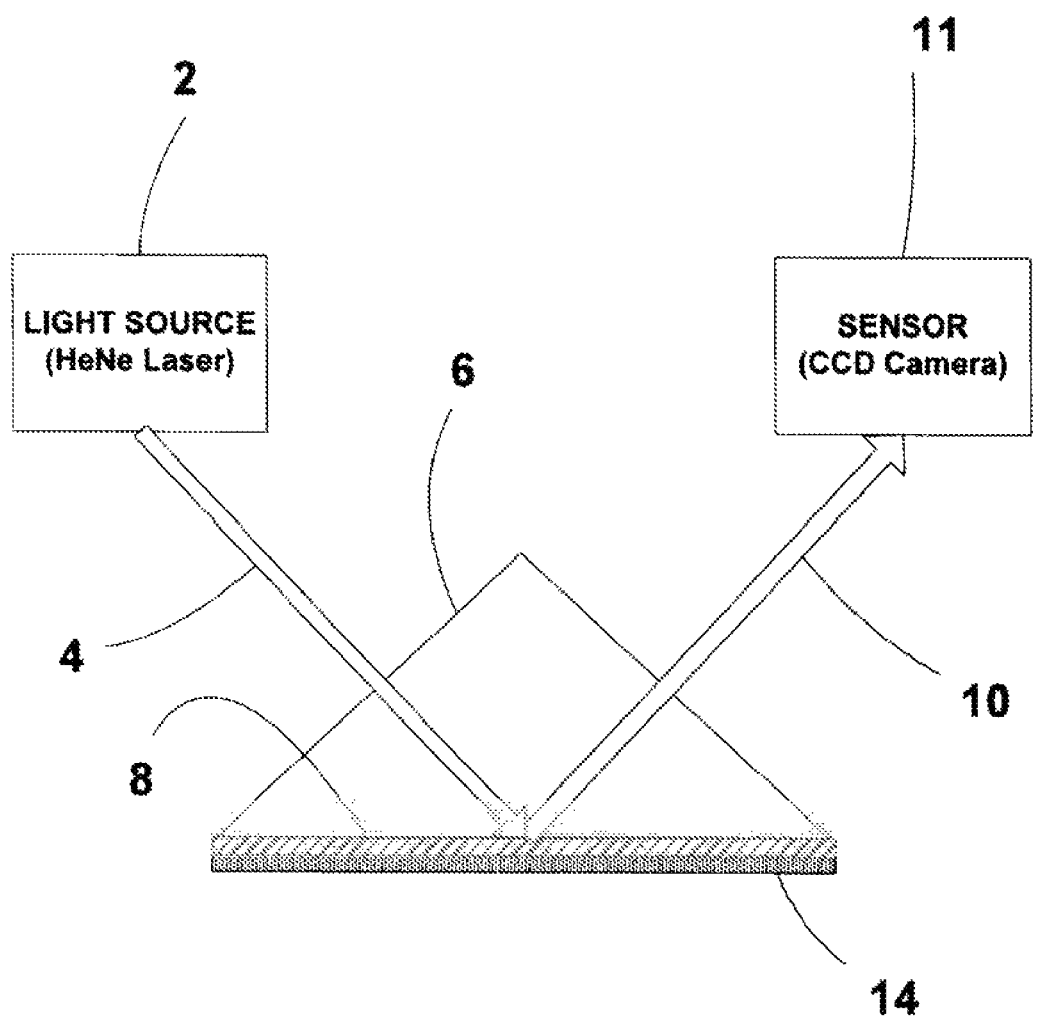
FIG. 1 is a diagram of an SPR sensor apparatus as per the Kretschmann configuration.

An example of the latter is shown in FIG. 1. A source of incident radiation such as a light source 2, for instance a Helium Neon laser, directs an incident beam 4 toward an SPR apparatus, here shown as including a prism 6 having a metal layer 8. The incident beam 4 passes through the prism 6 and reflects off the metal layer 8, as a reflected beam 10. The incident beam 4 reflects off the metal layer 8 at a "spot", typically an area about one millimeter in diameter or on a side, in which the sensor can sense the adsorption of analyte. The reflected beam 10 goes to a sensor 11, here shown as a charge-coupled device (CCD) camera.

In this configuration, adsorbed material 14 is on the side of the metal layer 8 opposite to the prism and the incident beam 4. The photons of the incident beam 4 that are incident at a certain angle, called the "SPR angle," are able to excite surface photons on the adsorbate side of the metal layer 8. Such excitation consumes the incident photon, producing a dip in the reflectivity of the sensor and an attenuation of the reflected beam 10 at that specific angle. The sensor 11 is used to measure the dip, and associated apparatus (not shown) also measures the angle. The SPR angle is dependent on the refractive index of the adsorbate 14, so in effect, the refractive index of the adsorbate 14 can be measured.

With conventional SPR sensors, the properties of the resonance are additionally determined by the refractive indices of the prism 6 and the adsorbate 14, and by the dispersion properties of the metal layer 8. For example, the width of the resonance, which affects the sensitivity with which shifts of the resonance can be observed, is fixed by these properties. Likewise, the amount of resonance shift in angle or wavelength due to changes in the sensed refractive index is fixed, resulting in a fixed dynamic range for the measurement. Based on these factors, the performance of a given apparatus can be characterized quantitatively in terms of a figure of merit (FOM). One such FOM is described below.

Additional limitations on conventional SPR sensor performance are the following:

1. Only one polarization of light, transverse magnetic (TM), experiences this SPR resonance. (By contrast, sensors having dielectric layers also may experience SPR resonance with transverse electric (TE) radiation, as will be described below.)

2. The metal films on the gratings and the prism can be damaged rather easily through contact with other materials. For instance, silver, which is sometimes used in SPR sensors, corrodes in air.

3. Conventional sensor structures limit the ability to optimize a figure of merit (FOM) for the sensor's performance. This will be further discussed below.

A Single Dielectric Layer

To address the above-listed issues, a dielectric layer has been placed between the metal film 8 and the adsorbate 14 to be sensed, to tune (optimize) the resonant properties of an SPR sensor. See Salamon et al., U.S. Pat. No. 5,991,488, "Coupled Plasmon-Waveguide Resonance Spectroscopic Device and Method for Measuring Film Properties." See also Ctyroky, Homola et al., "Tuning of Spectral Operation range of a waveguide surface plasmon resonance sensor"; and Knoll, "Interfaces and Thin Films as Seen by Bound Electromagnetic Waves".

These references describe the use of a single dielectric layer, also called an "overlayer," superimposed on the metal film. Structures having single layer dielectrics exhibit the property called "coupled plasmon waveguide resonance". In other words, the plasmon assists in coupling radiation into the dielectric waveguide mode. By adjusting the thickness of the dielectric overlayer, the sensors described in the references attempt to achieve some desirable property of the sensor that is not present without a dielectric layer, e.g., larger dynamic range, enhanced sensitivity, etc.

For instance, a figure of merit (FOM) for an SPR measurement system that measures adsorption of biomolecules depends on the particular method and application being used. In a situation in which 1) the dominant noise in the system is a random optical noise such as shot noise, and 2) the required measurement range is larger than the width of the resonance, one formula for a figure of merit is $$FOM = \frac{d\theta/dx}{\sqrt{FWHM \times scanrate}}$$

The greater the FOM value, the more accurate and sensitive is the sensor employing this SPR apparatus. In this expression, the numerator, $d\theta/dx$, represents the amount of shift in the resonance angle $\theta$ as a function of the adsorption $x$ of the analyte. The adsorption $x$ may be expressed in terms of the mass of adsorbed analyte per unit surface area. In general, there is a proportionality between adsorption and refractive index. For instance, an adsorption of 1 picogram per square millimeter of sensor surface area may correspond with a refractive index of $1 \times 10^{-6}$. The larger the value of the expression $d\theta/dx$, the greater the responsiveness of the measurement. FWHM is the full-width at half the maximum of the dip. The smaller that width, the sharper the dip, and the greater the resolution of the sensor. The scan range in the formula represents the angular scan range required to achieve a desired range of refractive indices that can be measured for the measurement (in terms of refractive index units, for example). This range of measurable refractive indices is referred to as the "dynamic range" of the apparatus.

The sensitivity of the system in this case is proportional to its FOM. With a single dielectric layer on the metal layer, it is possible to significantly reduce the FWHM of the resonance. However, at the same time, the $d\theta/dx$ variable typically is reduced, by an amount such that the FOM is not significantly changed.

A narrow FWHM may lead to an improvement in the FOM, for instance of roughly 30%. Unfortunately, these extremely narrow resonances, such as less than 0.1 degree, result from waveguide modes that propagate over longer distances, thus reducing the spatial resolution possible for the measurement. So, while it is possible to make resonances with less than 0.1 degree FWHM, the sample spot required to take advantage of this narrow resonance must be roughly 1 cm long. This is long enough to limit the development of practical and cost-effective multiplexing methods that conserve sample volumes and enable high-throughput measurements. Rather, these goals are facilitated by using arrays of sample spots with smaller sizes, for instance on the order of one millimeter.

Polarization may be either transverse magnetic (TM) or transverse electric (TE). For a given incident angle and/or incident light wavelength, one of these forms of polarization may experience the SPR dip in reflected light, but not the other. Rather, the other may experience its SPR at a much different incident angle or wavelength. To measure both, then, a sufficiently large range of incident angles and/or wavelengths must be tested to cover both of the critical values. This increases the time and cost of SPR sensing.

U.S. Pat. No. 5,991,488 teaches enhanced sensitivity with single dielectric layers used to reduce the FWHM of the resonance, but this enhanced sensitivity does not hold in the situation described above, where shot noise dominates and angular measurement range is greater than resonance width, which is typically the case for a general-purpose sensor. For one type of dielectric on the surface, increased sensitivity is only realized when the required dynamic range is less than the resonance width, and when the spot size of the sample is sufficiently large. The FWHM is typically determined primarily by the amount of ohmic loss in the dielectric film, and the ohmic losses limit the propagation length of the plasmon wave. This propagation length limits the spatial resolution, and thus the minimum spot size of a sample, available to an SPR instrument.

Performance of sensors having single dielectric layers is limited, in that very narrow angular resonances require similarly narrow spectral properties. Lasers or light sources with narrow (<1 nm) resonances are required to accurately measure these resonances. A broader, 30-nm, incoherent source, such as an LED would not give accurate measurements of the resonance shapes or position, and would reduce the sensitivity of the system.

Multiple Layers

Figure 2:
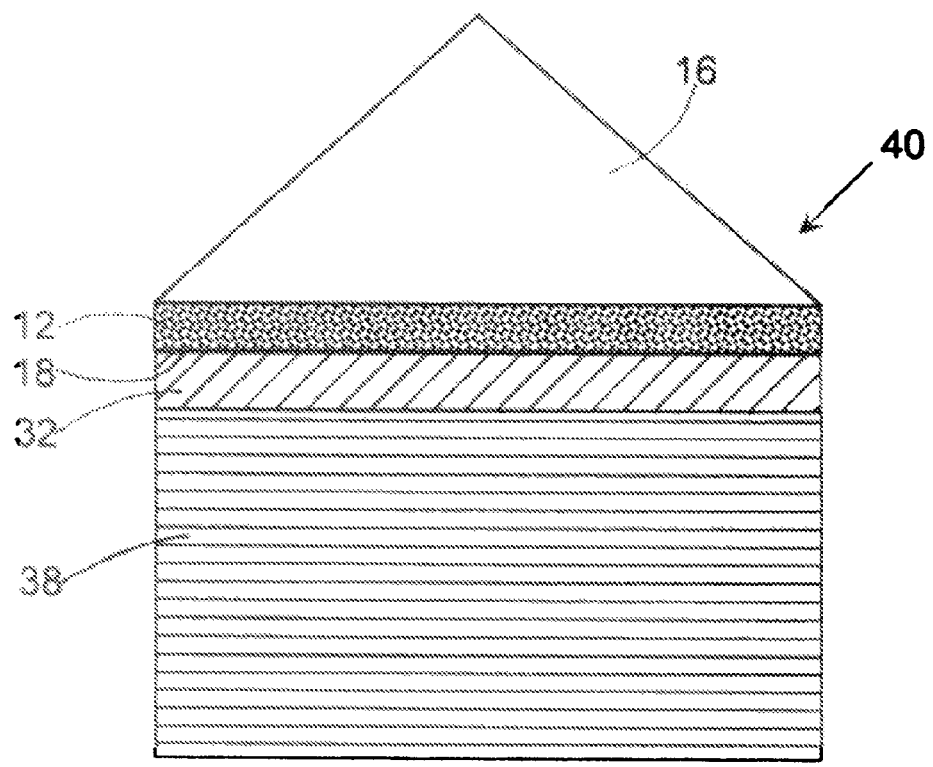
FIG. 2 is a diagram of a prior art apparatus, reproduced from FIG. 4 of Salamon et al., U.S. Pat. No. 5,991,488.

The '488 patent also makes reference to the possible use of more than one dielectric layer. FIG. 2 of the present patent application is a reproduction of FIG. 4 of the '488 patent, showing a sensor apparatus 40 including a prism 16, a metal layer 12 having a surface 18 abutting a first dielectric layer 32.

A second dielectric layer 38 abuts the first dielectric layer 32 at a side opposite to the side abutting the metal layer 12.

Figure 4:
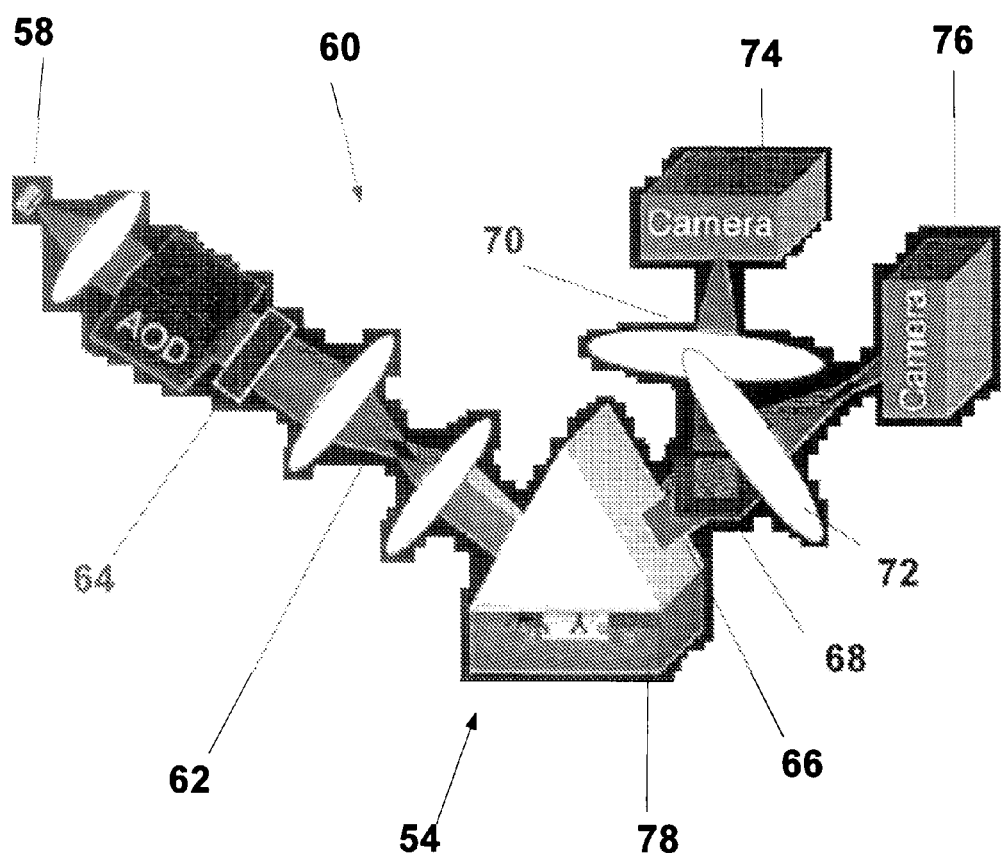
FIG. 4 is a diagram of a system employing an SPR sensor apparatus embodying the invention.

(Note, incidentally, that the second dielectric layer 38 of the '488 patent's FIG. 4 was drawn with what appears to be horizontal cross-hatching, reproduced in the present FIG. 2. Based on the horizontal cross-hatching, the single reference number 38, and the accompanying text in the '488 patent, it appears that 38 represents only one second layer, rather than a plurality of layers distinct from the first layer 32.)

The '488 patent gives certain specific descriptions of the layers 32 and 38, starting at its column 6, line 64, as follows:

"One 50 nm layer 32 of $TiO_2$ ($n_d$=2.2789, $k_d$=0.000151) protects the silver film 12; a second 750 nm layer 38 of a lower density, lower refractive index (n=1.35) dielectric material ($Na_3AlF_6$) is applied over the first layer. In this example this material is selected with a lower density and a correspondingly higher porosity so as to provide a structural matrix for adsorbing and immobilizing the sensing materials 20 (hydrogels are well known materials used for this purpose)."

From this teaching, a person of ordinary skill in the art would understand the '488 patent as being directed toward increasing the amount of analyte material that can bind to the sensor surface, rather than toward optimizing the sensitivity, FOM, or any other aspect of the sensor itself.

EMBODIMENTS OF THE INVENTION

Optimized Multiple Layers

In an embodiment of the invention, the sensitivity and dynamic range of surface plasmon resonance is enhanced, relative to that of a conventional sensor apparatus having a metal layer and just one dielectric layer.

In an embodiment of the invention, alternating high and low index dielectric layers on the side of the conductive layer opposite the incident radiation operate as a distributed Bragg reflection (DBR) stack. Also, the boundary surface of the last dielectric layer (that is, the outer boundary surface, where the analyte sample would be) has a refractive index such that the incident radiation is completely reflected (except for factors such as scattering due to surface irregularities) according to the well known optical phenomenon called total internal reflection."

For the purpose of this description of embodiments of the invention, we will say by convention and without limitation that the layer of dielectric which is farthest from the conductive layer and is adjacent to the adsorbed sample will be called the "last" dielectric layer, as above. Likewise, the "first" dielectric layer is the dielectric layer immediately adjacent to the conductive layer. A "penultimate" (i.e., second-last) dielectric layer, is the dielectric layer adjacent to the last dielectric layer.

The conductive layer serves to couple the light into waveguide modes propagating in the dielectric stack. Without the conductive layer, the incident radiation would not be able to couple into the dielectric stack at angles for which the resonance phenomenon occurs. The radiation that penetrates the conductive and dielectric layers, and then reflects off of the last layer, passes back through the dielectric layers. Since these operate in a manner similar to a DBR stack, they are also a mirror. The effect is to create a resonator between the DBR stack and the TIR of the last layer. The energy of the radiation tends to be trapped within the resonator, although a part of the energy is lost due to the conductivity of the conductive layer, or to passing back out of the prism as the reflected beam.

The trapped wave is basically a waveguide mode. Since the energy is primarily trapped within the dielectric layers, rather than within the conductive layer, only a small amount of the energy, that which is present in the conductive layer, contributes to loss. The low loss gives a higher-Q resonator, which results in more sensitivity, more dynamic range, or both.

An embodiment of the invention allows the possibility of both transverse electric (TE) and transverse magnetic (TM) polarized light providing information about the conformation and birefringence of an adsorbed biomolecular layer. A given stack of dielectric layers will produce multiple resonances each, for TM and TE radiation. The incident angles and wavelengths of the resonances for the two types of polarization may be manipulated by selecting appropriate thicknesses and indices of refraction for the dielectric layers. In so doing, it is possible to co-locate resonances; that is, one of the resonances for each type of polarization can be made to resonate (i) at the same incident angle or within a narrow range of incident angles, or (ii) at the same wavelength or within a narrow range of wavelengths. Thus, in a scanning angle (that is, incident angle) or wavelength configuration, only a relatively narrow range of incident angles or wavelengths must be utilized in order to obtain readings for both forms of polarization.

By contrast, with conventional sensor configurations such as a single dielectric layer, the TE and TM resonances occur at different angles and wavelengths as noted above, thus requiring a scan of a wider range of incident angles to scan one of each, and making simultaneous measurement of both very difficult.

The FOM derived above is appropriate for a system in which a predetermined dynamic range is required. As noted above, a single dielectric layer cannot change the FOM (and thus the sensitivity) significantly, because the de/dx variable diminishes as the FWHM does, so that the FOM doesn't significantly change. The resonance shape may become narrower, but almost no additional sensitivity is realized because, as noted above, $d\theta/dx$ also gets smaller. However, in an embodiment of the present invention, specification for multiple dielectric layers are provided, which enhance the sensitivity of an SPR instrument, while preserving a practical spot size and either preserving or enhancing the dynamic range.

For example, a combination of two dielectric layers in which the highest index material is farthest from the metal film can give enhanced sensitivity (improvements in the FOM). Many waveguide modes can exist in the dielectric layers, and by choosing one of these modes in which the intensity of the light is relatively small in the metal layer, it is possible to make a resonance with an extremely small FWHM without the reduction in $d\theta/dx$. In particular, in an embodiment of the invention, the dielectric stack has a waveguide mode such that an intensity of radiation in the metal layer is sufficiently small that the resonance has a reduced full-width at half the maximum of the dip (FWHM). The rate of change in an amount of shift in the resonance angle $\theta$ relative to the adsorption x of the analyte substance on the surface (that is, $d\theta/dx$) is maintained. In an embodiment it is even possible to increase $d\theta/dx$, but if it is not at least maintained, it should not decrease by an amount greater than the square root of the reduction in FWHM.

An SPR sensor apparatus embodying the invention includes layers of dielectric materials (herein also called "dielectric layers" or merely "layers") with different indices of refraction, collectively called a "dielectric stack". However, the number of such dielectric layers may vary. Also, the quantitative values of the indices of refraction may vary. Where we say the index of refraction of a given dielectric layer is "high" and "low", the terms mean "high" and "low" relative to those of the adjacent layer or layers, without other limitation as to the values or magnitudes of the indices of refraction.

In general, successive layers of a dielectric stack have alternating high and low refractive indices. Also in general, the last dielectric layer of the dielectric stack of an SPR sensor will have a high index of refraction (that is, higher than that of the penultimate dielectric layer). Given that the dielectric layers have alternatingly high and low indices, in general the first layer will be low if the number of layers is even, and high if the number is odd.

A sensor may be optimized for either TM or TE radiation based on the thicknesses, refractive indices, etc., of the respective layers, or the optimization may be adjusted for a desired balance between these two forms of polarization. One factor in the optimization is the number of layers. As discussed below, even and odd numbers of layers relate to optimization for sensing TM or TE radiation, and the choice of the number of layers may be used to optimize for one form of polarization, as against the other. However, other factors such as layer thicknesses and refractive indices may balance out optimization for both forms of polarization, or even swing the optimization to the other form of polarization. Typically, more layers result in a higher FOM, but large numbers of layers can be difficult to manufacture reliably.

Subject to the above, for sensing TM polarized light, embodiments of the invention may have an odd number of dielectric layers, such that the first and last layers' indices of refraction are both high. The number of dielectric layers may vary. In embodiments of the invention the layer structures have refractive indices in the following sequences: high-low-high, or high-low-high-low-high, or with even more repetitions.

In another embodiment of the invention, groups of adjacent layers may be treated collectively as "effective layers", and such collective treatment may afford us another basis for characterizing the layers by their indices of refraction. For instance, a group of adjacent dielectric layers may have the following relative indices of refraction: very high, high, very high, low, very low, low. That is, a first effective layer is made up of the three layers with very high, high, and very high indices ("very high" being higher than "high"). A second effective layer is made up of the three layers with low, very low, and low indices ("low" being not as low as "very low"). The resultant dielectric stack thus has two effective layers. Other embodiments of the invention may employ other variations on relative values of the refractive indices, different numbers of layers within an effective layer, etc.

For instance, consider a 200 nm thick structure comprising a low index 10 nm layer in between two high index 95 nm layers. The resultant three-layer 200 nm thick structure may be called an "effective layer". That effective layer would still have an effectively high index, and could be used in combination with other individual or effective layers in an embodiment of the invention.

Also subject to the above, for sensing TE polarized light, embodiments of the invention may have an even number of dielectric layers, such that the indices of refraction are low for the first layer and high for the last layer. Again, the number of layers may vary. For instance, an embodiment of the invention may employ a series of low-high or low-high-low-high layers (or some with even more repetition). Again, additional embodiments may be implemented, employing the concept of generalizing to one or more "effective layers" as described above.

In an embodiment, the width of the resonance cannot be too narrow because the sample spots in our multiplexed array are preferably on the order of 1 mm in size. Also, the camera's frame-rate is limited and consequently too-narrow resonances might be under-sampled in a large scan range. The limitations described in this paragraph are specific to certain embodiments of the invention, and may not be present in the same form in other embodiments. However, they may be representative of more general limitations. For example, some embodiments of SPR apparatus may not use a camera. However, a narrow resonance requires an ability to make high resolution measurements of angle, so embodiments achieving such a narrow resonance generally will employ a camera or other high resolution measurement apparatus.

Interfaces between layers behave as per the Fresnel reflection formulas. These interfaces also include the prism-to-metal interface, and the metal-to-dielectric interface, as well as the various dielectric interfaces. By summing up the contributions to the reflection from all of these interfaces, the sensor's reflectivity can be calculated.

Figure 3:
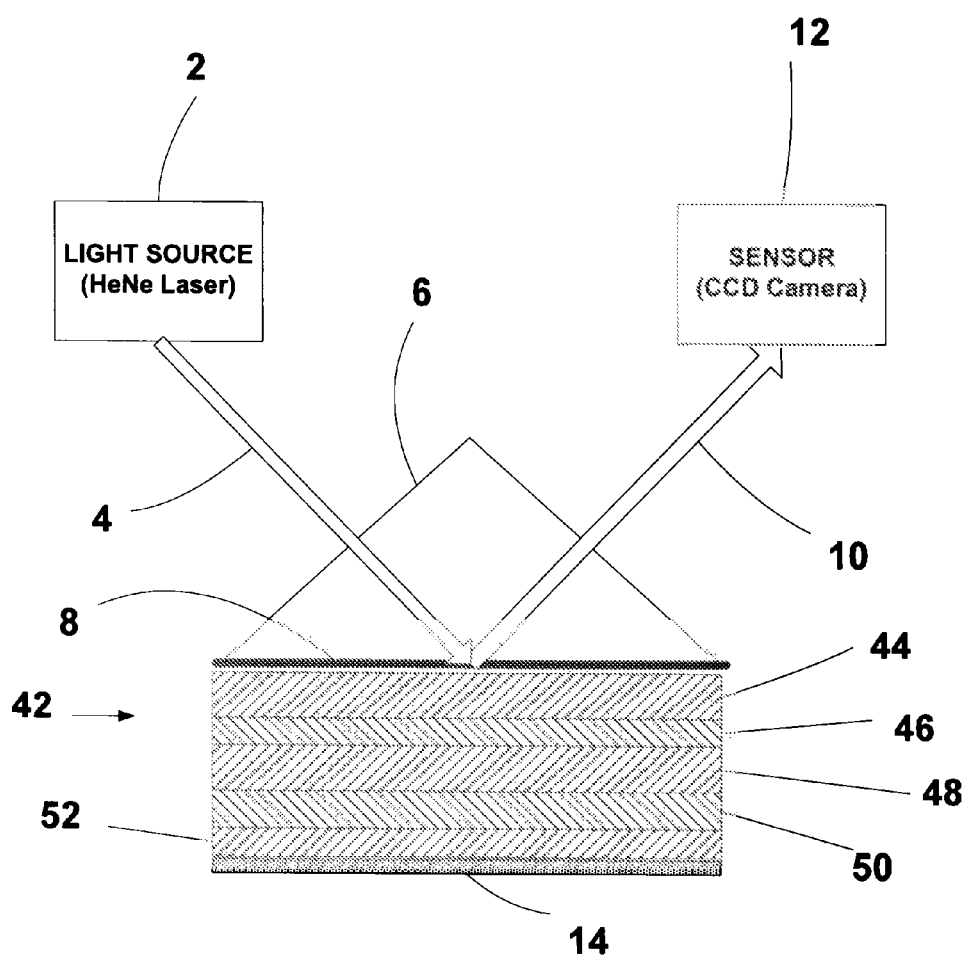
FIG. 3 is a diagram of an apparatus embodying the invention.

An exemplary SPR sensor embodying the invention is shown in FIG. 3. Elements 2, 4, 6, 8, 10, 12, and 14 similar to those of FIG. 1 are numbered correspondingly. However, a stack 42 of dielectric layers is disposed on the side of the metal layer 8 opposite to that of the incident beam 4.

The stack 42 includes alternating layers of high and low refractive index. They are configured in an analog to a distributed Bragg reflection (DBR) stack to create waveguide modes in the stack that minimize light in the metal film, where the loss is greatest, and to maximize light in the outermost layer 50. This gives sensitivity to the adsorbed analyte 14 onto the surface of the stack 52 due to a biomolecular interaction. Embodiments may have a dielectric stack which is optimized for distributed Bragg reflection. In one such embodiment, each layer has a thickness on the order of one half of the wavelength of light in that material. For example, a low index layer might optimally be 250 nm. Nearly the same effect could be obtained by a low index layer 124 nm thick, followed by a high index material 2 nm thick, followed by another low index material 124 nm thick. This is effectively a low index layer 250 nm thick.

In the example of FIG. 3, the stack 42 includes five dielectric layers 44, 46, 48, 50, and 52, disposed on the side of the metal layer 8 opposite to that receiving the incident beam 4. The layers 44, 48, and 52 are made of a material having a relatively high index of refraction, such as silicon nitride The layers 46 and 50 are made of a material having a relatively low index of refraction, such as silicon dioxide, $SiO_2$.

To achieve the optimization, one example gives dielectric layer thicknesses as follows: The layer 44 is formed of silicon nitride using a plasma-enhanced chemical vapor deposition process (PECVD) process and is 2250 Angstroms in thickness. The PECVD process adds some hydrogen to the silicon nitride to produce SiNH, and the silicon nitride compound is often written in that form, as SiNH. Embodiments of the invention may employ silicon nitride compounds, not necessarily limited to the specific form SiNH. The layer 46 is formed of $SiO_2$ and is 1500 Angstroms in thickness. The layer 48 is formed of silicon nitride and is 2250 Angstroms in thickness. The layer 50 is formed of $SiO_2$ and is 1500 Angstroms in thickness. The layer 52 is formed of silicon nitride and is 1100 Angstroms in thickness.

FIG. 4 is a diagram depicting a system for simultaneous measurement of TE and TM light. An SPR sensor apparatus 54, generally as shown in FIG. 3, is provided. Also shown are a light source 58 and optics 60 for producing an incident beam 62 that is directed into the SPR sensor apparatus 54. The optics 60 include a half-wave plate 64, for rotating the incident beam 62, for instance by 22 degrees.

A reflected beam 66 is split by a polarizing beam splitter 68, to separate the TE and TM components of the reflected beam 66. The components pass light to separate radiation detectors that receive the TE and TM light separately. In the example of FIG. 4, these are shown as separate optics 70 and 72, and respective separate sensors (e.g., CCD cameras) 74 and 76, that receive the TE and TM light separately.

The SPR sensor apparatus 54 of FIG. 4 contains a dielectric stack 78, having a number of layers, with respective thicknesses and refractive indices, so as to enable at least one each of the TE and TM resonances to be co-located in wavelength, incident angle, etc. This co-location of TE and TM resonances makes it easier simultaneously to scan both resonances, and to construct a real-time measurement of both resonances.

With non-optimized thicknesses, such sensitivity enhancements are not achieved. For example, a model system with a high index layer between the metal layer and a low index last layer can provide enhanced sensitivity, but with significant tradeoffs. A single $SiO_2$ dielectric layer more than a micron thick, when not optimized, can give a sensitivity enhancement of just 30%. With thinner layers of $SiO_2$, that number is even smaller. To achieve this enhanced sensitivity, the resonance width is reduced to ~0.1 mm. Consequently, a spot size on the sensor would have to be larger than 1 mm (in the plasmon propagation direction) in order to be clearly resolved.

With optimization and using the same types of materials, a sensitivity enhancement of ~250% is possible, with a total dielectric thickness of just 0.56 microns. Furthermore, the FWHM of the resonances is 0.395 degrees, which is quite sufficiently wide for 1 mm spot sizes. Smaller spot sizes preserve the ability to multiplex the spots easily.

The ability to measure resonances for both TE and TM polarized light allows additional information to be obtained. For instance, the system of FIG. 4 may additionally include apparatus (not separately shown) for measuring at least one of (i) a mass of an adsorbed layer, (ii) a density of an adsorbed layer, (iii) a thickness of an adsorbed layer, and (iv) anisotropic properties of an adsorbed layer. Self-referencing is possible, because the bulk index of refraction contributions can now be distinguished from the adsorption.

As noted above, a conventional SPR sensor detects changes in the refractive index of material on the back side of the prism's metal layer. Refractive index changes derive from three possible sources: 1) temperature changes of the fluid carrying samples to the sensor, 2) changes in the bulk index of refraction of the fluid due to changes in the concentration of dissolved solids, such as salts, etc., and 3) adsorption of analyte to the sensor surface. Where the third contribution is of interest, a reference sensing location (spot) is employed in which no analyte is adsorbed. It measures contributions from sources 1) and 2), and so the difference between the refractive index variations of the reference spot and the actual sample spot is taken. This difference provides the contribution 3) that is of interest.

Self-referencing makes it possible to omit the use of a reference spot. The actual shifts of the co-located TE and TM resonances have different proportionality constants for shifts due to adsorption and shifts due to bulk index of refraction changes. By measuring both changes, and using some calibration derived factors, we can solve an equation to determine two unknowns—the amount of adsorption and the amount of bulk refractive index change. This accomplishes the goal described above of determining the contribution 3) above.

Also, anisotropic properties such as birefringence and linear dichroism can be detected with the multiple layers. This information can be used to derive the degree of order in a lipid bilayer, for example, or the conformational change of an enzyme as a small molecule binds to it.

The dielectrics can be deposited onto the metal layer using any of a variety of dielectric deposition techniques, such as plasma-enhanced chemical vapor deposition (PECVD), etc. Any relatively transparent dielectric material should be acceptable with these ideas. Some examples cited in U.S. Pat. No. 5,991,488, which may also be employed in embodiments of the invention, include $SiO_2$, $TiO_2$, $MgF_2$, $Al_2O_3$, $LaF_3$, $Na_3AlF_6$, etc.

Although the present invention has been described in detail with reference to particular embodiments, persons possessing ordinary skill in the art to which this invention pertains will appreciate that various modifications and enhancements may be made without departing from the spirit and scope of the claims that follow.

What is claimed is:

1. A surface plasmon resonance (SPR) spectrometer sensor apparatus for measuring a property of an analyte substance that can be adsorbed on a surface by directing a beam of incident radiation on the apparatus at an incident angle relative thereto, receiving a beam of reflected radiation off the apparatus, and measuring dips in reflected polarized radiation as a function of at least one of incident angle and wavelength, each of the dips being indicative of a resonance in the apparatus, the SPR spectrometer comprising:

a metal layer having a first side which receives incident radiation, and having a second side opposite to the first side; and a dielectric stack, having first and second sides opposite to each other, the first side being in contact with the conductive layer, the second side for receiving an analyte sample to be disposed thereon;

the dielectric stack including a plurality of dielectric layers having respective thicknesses and indices of refraction, each successive one of the plurality of dielectric layers having an index of refraction which is alternatingly higher than, and lower than, the indices of refraction of adjacent ones of the plurality of dielectric layers;

the plurality of dielectric layers including a first dielectric layer at the first side of the dielectric stack, and a last dielectric layer at the second side of the dielectric stack, the last dielectric layer having a boundary surface for contacting the received analyte sample, and having an index of refraction so as to achieve total internal reflection (TIR) at the boundary surface;

wherein the dielectric stack includes:

(i) a first dielectric layer, having a first index of refraction, at the first side of the dielectric stack and disposed on the second side of the metal layer;

(ii) a second dielectric layer disposed on the first dielectric layer, the second dielectric layer having a second index of refraction less than the first index of refraction; and (iii) a third dielectric layer disposed on the second dielectric layer, the third dielectric layer having a third index of refraction greater than the second index of refraction; and a prism having a surface disposed on the first side of the conductive layer opposite the second side of the metal layer, which second side of the metal layer is in contact with the dielectric stack, wherein the metal layer receives the incident radiation after passing through a portion of the prism including a second surface thereof, wherein the incident radiation is reflected from the metal layer, and wherein the reflected radiation emerges out of the prism from a third side thereof.

2. An apparatus as recited in claim 1, wherein:
the plurality of dielectric layers further includes a penultimate dielectric layer adjacent to and in contact with the last dielectric layer; and the penultimate dielectric layer has an index of refraction lower than that of the last dielectric layer.

3. An apparatus as recited in claim 1, wherein:
the reflected polarized radiation includes at least one of transverse magnetic (TM) and transverse electric (TE) polarized radiation; and
the respective thicknesses and indices of refraction of the dielectric layers are such that a resonant angle of incidence of TM polarized radiation and a resonant angle of incidence of TE polarized radiation are co-located.

4. An apparatus as recited in claim 1, wherein the third dielectric layer is the last dielectric layer.

5. An apparatus as recited in claim 1, wherein the dielectric stack includes:
(i) a first dielectric layer, having a first index of refraction, at the first side of the dielectric stack and disposed on and immediately adjoining the second side of the metal layer;
(ii) a second dielectric layer disposed on and immediately adjoining the first dielectric layer, the second dielectric layer having a second index of refraction greater than the first index of refraction;
(iii) a third dielectric layer disposed on and immediately adjoining the second dielectric layer, the third dielectric layer having a third index of refraction less than the second index of refraction; and
(iv) a fourth dielectric layer disposed on and immediately adjoining the first dielectric layer, the second dielectric layer having a second index of refraction greater than the third index of refraction.

6. An apparatus as recited in claim 5, wherein the fourth dielectric layer is the last dielectric layer.

7. An apparatus as recited in claim 1, wherein the dielectric stack includes a first effective layer and a second effective layer adjacent to each other, the first effective layer including a first set of adjacent layers, the second effective layer including a second set of adjacent layers.

8. The apparatus of claim 1, wherein the dielectric stack is not in contact with the first side of the metal layer receives the incident radiation.

9. A surface plasmon resonance (SPR) spectrometer for measuring a property of an analyte substance that is adsorbed on a surface by directing a beam of incident radiation on the apparatus at an incident angle relative thereto, receiving a beam of reflected radiation off the apparatus, and measuring a dip in reflected radiation as a function of at least one of incident angle and wavelength, the dip being indicative of a resonance in the apparatus, the SPR spectrometer comprising:
(A) an SPR spectrometer sensor apparatus that comprises:
an electrically conductive layer having a first side which receives incident radiation, and having a second side opposite to the first side; and
a dielectric stack, having first and second sides opposite to each other, the first side being in contact with the electrically conductive layer, the second side for receiving an analyte sample to be disposed thereon;
the dielectric stack including a plurality of dielectric layers having respective thicknesses and indices of refraction, each successive one of the plurality of dielectric layers having an index of refraction which is alternatingly higher than, and lower than, the indices of refraction of adjacent ones of the plurality of dielectric layers;
the plurality of dielectric layers including a first dielectric layer at the first side of the dielectric stack, and a last dielectric layer at the second side of the dielectric stack, the last dielectric layer having a boundary surface for contacting the received analyte sample, and having an index of refraction so as to achieve total internal reflection (TIR) at the boundary surface;
wherein the dielectric stack includes:
(i) a first dielectric layer, having a first index of refraction, at the first side of the dielectric stack and disposed on and in contact with the second side of the electrically conductive layer;
(ii) a second dielectric layer disposed on and in contact with the first dielectric layer, the second dielectric layer having a second index of refraction less than the first index of refraction; and
(iii) a third dielectric layer disposed on and in contact with the second dielectric layer, the third dielectric layer having a third index of refraction greater than the second index of refraction; and
(B) a polarizing beam splitter disposed in a path of the beam of reflected radiation, for splitting the beam of reflected radiation into two beams of different polarizations;
(C) a first radiation detector for receiving TM polarized radiation from the reflected radiation and measuring a dip therein; and
(D) a second radiation detector for receiving TE polarized radiation from the reflected radiation and measuring a dip therein.

10. An SPR spectrometer as recited in claim 9, wherein the polarizing beam splitter splits the beam of reflected radiation into two beams of transverse magnetic (TM) and transverse electric (TE) polarization.

11. An SPR spectrometer as recited in claim 9, wherein:
the plurality of dielectric layers further includes a penultimate dielectric layer adjacent to the last dielectric layer; and
the penultimate dielectric layer has an index of refraction lower than that of the last dielectric layer.

12. An SPR spectrometer as recited in claim 9, wherein:
the reflected polarized radiation includes at least one of transverse magnetic (TM) and transverse electric (TE) polarized radiation; and
the respective thicknesses and indices of refraction of the dielectric layers are such that a resonant angle of incidence of TM polarized radiation and a resonant angle of incidence of TE polarized radiation are co-located.

13. An SPR spectrometer as recited in claim 9, wherein the dielectric stack has a waveguide mode such that an intensity of radiation in the metal layer is sufficiently small that the resonance has a reduced full-width at half the maximum of the dip (FWHM).

14. An SPR spectrometer as recited in claim 9, wherein the dielectric stack includes a first effective layer and a second effective layer adjacent to each other, the first effective layer including a first set of adjacent layers, the second effective layer including a second set of adjacent layers.

15. The SPR spectrometer of claim 9, wherein the electrically conductive layer is a metal layer.

16. A surface plasmon resonance (SPR) spectrometer sensor, comprising:

an electrically conductive layer having a first side which receives incident radiation, and having a second side opposite to the first side; and a dielectric stack disposed entirely on the second side of the electrically conductive layer, the dielectric layer having first and second sides opposite to each other, the first side of the dielectric stack being in contact with the second side of the conductive layer, the second side of the dielectric stack being configured to have an analyte sample to be disposed thereon, wherein the dielectric stack includes a plurality of dielectric layers having respective thicknesses and indices of refraction, each successive one of the plurality of dielectric layers having an index of refraction which is alternatingly higher than, and lower than, the indices of refraction of immediately adjoining ones of the plurality of dielectric layers, and wherein the plurality of dielectric layers includes:
  a first dielectric layer at the first side of the dielectric stack,
  a last dielectric layer at the second side of the dielectric stack, and
  a penultimate dielectric layer disposed between the first and last dielectric layers and immediately adjoining the last dielectric layer,
wherein the last dielectric layer has a boundary surface configured to contact the received analyte sample, and has an index of refraction which is greater than an index of refraction of the immediately adjoining penultimate dielectric layer.

* * * * *